United States Patent [19]

Dyke

[11] Patent Number: 5,059,184

[45] Date of Patent: Oct. 22, 1991

[54] HYPODERMIC NEEDLE APPARATUS

[76] Inventor: Timothy J. Dyke, 17 Minute Man La., Lexington, Mass. 02173

[21] Appl. No.: 518,603

[22] Filed: May 3, 1990

[51] Int. Cl.$^5$ ............................................. A61M 5/32
[52] U.S. Cl. ..................................... 604/198; 604/263
[58] Field of Search ................ 604/192, 197, 198, 263

[56] References Cited

U.S. PATENT DOCUMENTS

| | | | |
|---|---|---|---|
| 4,801,295 | 1/1989 | Spencer | 604/198 |
| 4,826,490 | 5/1989 | Byrne et al. | 604/198 |
| 4,826,491 | 5/1989 | Schramm | 604/198 |
| 4,842,587 | 6/1989 | Poncy | 609/198 |
| 4,850,977 | 7/1989 | Bayless | 604/198 |
| 4,874,384 | 10/1989 | Nonez | 604/198 |
| 4,894,055 | 1/1990 | Sudnak | 604/198 |
| 4,923,447 | 5/1990 | Morgan | 604/198 |

*Primary Examiner*—Stephen C. Pellegrino
*Assistant Examiner*—Michael Rafa
*Attorney, Agent, or Firm*—Henderson & Sturm

[57] ABSTRACT

A hypodermic needle apparatus (10) equipped with a latching unit (14) for selectively immobilizing a pair of sheath members (18, 23) relative to a needle (16) such that one of the sheath members (23) may be temporarily retracted to expose the needel (16) and then extended and permanently immobilized in a covering relationship relative to the tip of the needle (16).

6 Claims, 1 Drawing Sheet

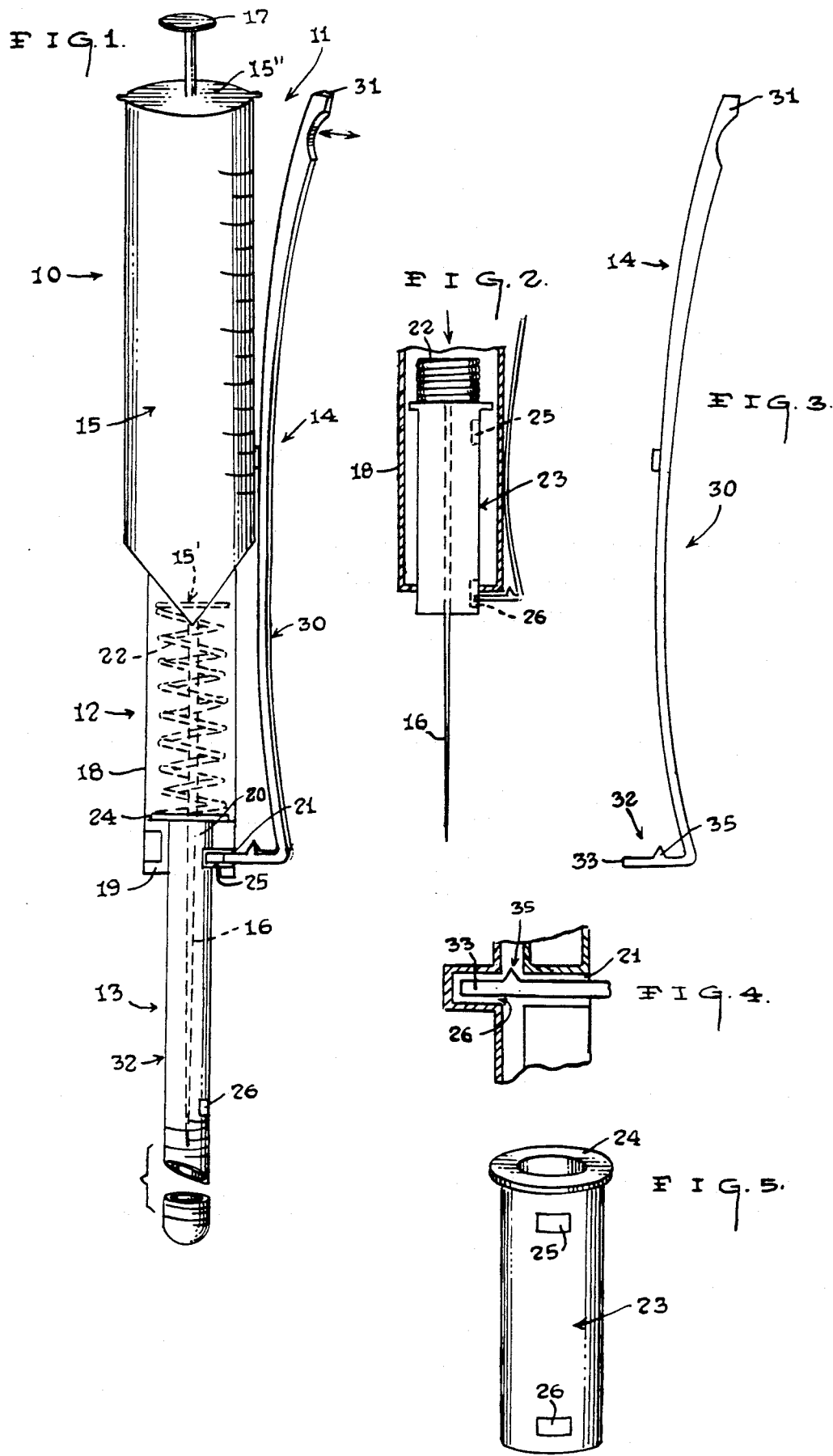

5,059,184

HYPODERMIC NEEDLE APPARATUS

TECHNICAL FIELD

The present invention relates to the field of hypodermic needle constructions in general, and in particular to a locking arrangement for hypodermic needles wherein the locking apparatus can be selectively engaged in either the retracted or extended mode of disposition of the needle.

BACKGROUND ART

This invention was the subject matter of Document Disclosure Program Registration No. 237,591 which was filed in the United States Patent and Trademark Office on Oct. 23, 1989.

As can be seen by reference to the following U.S. Pat. Nos. 4,801,295; 4,826,491; 4,842,587; and 4,850,977; the prior art is replete with myriad and diverse hypodermic needle arrangements.

While all of the aforementioned prior art constructions are more than adequate for the basic purpose and function for which they have been specifically designed, these devices do not provide the ease of usage and the selective engagement of the locking mechanism that is embodied in the present invention.

It should further be emphasized that considering the health hazard that is posed by contaminated needles, any systems that allows a needle to be immobilized relative to its sheath after usage represents an advantage to mankind.

As a consequence of the foregoing situation, there has existed a longstanding need for a safe and secure way to render a hypodermic needle inoperative after an injection has taken place. The needle is enclosed within a protective sheath, and the provision of such a construction is a stated objective of the present invention.

DISCLOSURE OF THE INVENTION

Briefly stated, the hypodermic needle construction that forms the basis of the present invention comprises a conventional syringe body equipped with a needle and plunger for dispensing medication or drawing blood.

In addition, the syringe body is further provided with an upper and a lower sheath units which are spring biased and movable relative to one another. The syringe body is further provided with a latching unit that is adapted to both temporarily and permanently immobilize the sheath units relative to one another. The needle will be temporarily sheated prior to use to avoid the inadvertent pricking of an individual. Once the needle has been used for its intended purpose, the latching unit can be employed to permanently sheath the needle prior to the disposal thereof.

As will be explained in greater detail further on in the specification, the latching unit may also be deployed to immobilize the sheaths relative to the needle on either a temporary or permanent basis. The lower sheath is disposed in a retracted position relative to the upper sheath thereby leaving the needle in an exposed disposition relative to the sheaths.

BRIEF DESCRIPTION OF THE DRAWINGS

These and other attributed of the invention will become more clear upon a thorough study of the following description of the best mode for carrying out the invention, particularly when reviewed in conjunction with the drawings, wherein:

FIG. 1 is a perspective view of the hypodermic needle construction that forms the basis of the present invention;

FIG. 2 is a cross sectional view of the device with the needle in an exposed disposition;

FIG. 3 is a cross-sectional view of the device in the sheathed and locked disposition;

FIG. 4 is an enlarged detail view of the lower sheath unit; and

FIG. 5 is an enlarged isolated detail view of the latching unit.

BEST MODE FOR CARRYING OUT THE INVENTION

As can be seen by reference to the drawings, and in particular to FIG. 1, the hypodermic needle construction that forms the basis of the present invention is designated generally by the reference numeral (10). The construction (10) comprises in general, a conventional syringe unit (11) having a pair of relatively movable sheath units (12, 13) and a latching unit (14) for both temporarily and permanently immobilizing the sheath units (12, 13) relative to one another. These units will now be described in seriatim fashion.

As can best be seen by reference to FIG. 1, the conventional syringe unit (11) comprises a syringe reservoir body (15) equipped with a needle (16) on one end (15') and a plunger (17) on the other end (15").

As can also be seen by reference to FIG. 1, the sheath unit (12) comprises a first enlarged sheath member (18) connected on its upper end to the lower end (15') of the syringe body (15). The lower end of the first sheath member (18) is provided with a stepped shoulder (19) which surrounds the reduced diameter axial bore (20) of the sheath member (18). In addition, the lower end of the first sheath member (18) is further provided with a radially disposed aperture (21) whose purpose and function will be described presently. The first sheath member is also provided with an elongated spring member (22) whose purpose and function will likewise be explained shortly.

The second sheath unit (13) comprises an elongated relatively narrow second sheath member (23) whose lower end is dimensioned to fit within the reduced diameter axial bore (20) of the first sheath member (18). The upper end is provided with a radial flange (24) which is dimensioned to rest on the stepped shoulder (19) of the first sheath member and to provide a bearing surface of the spring member (22) to spring bias the second sheath member (23) away from the first sheath member (18).

Turning now to FIGS. 1 and 4, it can be seen that the second sheath member (23) is further provided with a plurality of spaced apertures (25, 26) whose purpose and function will be described presently.

In FIGS. 1 and 5, it can be seen that the latching unit (14) comprises an elongated latching lever (30) which is pivotally secured proximate to its midpoint to the syringe body (15). In addition, the upper end of latching ever (30) forms a lever handle (31) and the lower end of the latching ever (30) is provided with a catch member (32) which extends inwardly towards the sheath units (12, 13). The outer end (33) of the catch member (32) is dimensioned to be received in the radially disposed aperture (21) in the first sheath member (18) and a selected one of the apertures (25, 26) in the second sheath member (23). Furthermore, the catch member (32) is further provided with a deformable one-way tang (35) which is spaced from the outer end (33) of the catch member (32). The tang (35) may be forced inwardly through the aperture (21) in the first sheath member (18) such that once the tang (35) has passed through the aperture (21), it cannot be forced back through aperture (21) and the other end (33) of the catch member (32) will remain in registry with the selected aperture (25, 26) in the second sheath member (23) to permanently immobilize the second sheath member (23) relative to the first sheath member (18).

Turning now to FIGS. 1 through 3, it can be seen that prior to use, the outer end (33) of the catch member (32) is temporarily registered with the aperture (21) in the first sheath member (18) and the upper aperture (25) in the second sheath member (23). When the needle is to be exposed, the lower handle (31) is depressed to remove the outer end (33) of the catch member (32) from engagement with the second sheath member (23) to allow the second sheath member (23) to be retracted relative to the first sheath member (18) by overcoming the spring biasing exerted on the second sheath member (23) by the spring member (22).

It should also be noted that once the second sheath member (23) has been retracted relative to the first sheath member (18), the ever handle can be released to bring the outer end (33) of the catch member (32) into registry with the lower aperture (26) in the second sheath member (23) to temporarily immobilize the second sheath member (23) in its retracted position relative to the first sheath member.

Now, after the needle (16) has served its useful purpose, the ever handle (31) is once again depressed to remove the catch member (21) from engagement with the lower aperture (26) in the second sheath member (23) such that the second sheath member (23) will return to the position illustrated in FIG. 1 via the action of the spring member (22).

When the user wishes to permanently lock the second sheath member relative to the first sheath member (18), a that is necessary is to move the lever handle (31) away from the syringe body (15) to force the deformable tang (35) through the aperture (21) in the first sheath member (18) such that the outer end (33) of the catch member (32) is placed into permanent registry with the upper aperture (25) in the second sheath member (18).

By now it should be appreciated that in order to maintain the alignment between the apertures (21, 25, 26), this invention further contemplates the use of guide means (not shown) between the first (18) and the second (23) sheath members such that there will not be any relative rotation between the respective sheath members (18, 23) as the second sheath member (23) reciprocates relative to the first sheath member (18).

Having thereby described the subject matter of the present invention, it should be apparent that many substitutions and variations of the invention are possible in light of the above teachings. It is therefore to be understood that the invention as taught and described herein is only to be limited to the extent of the breadth and scope of the appended claims.

I claim:

1. A hypodermic needle apparatus including a syringe body having a plunger on the upper end and a needle on the lower end wherein the improvement comprises:
   a first sheath member having an upper end secured to the lower end of the syringe body and disposed in a surrounding relationship with respect to said needle; wherein
   the first sheath member is provided with a radially disposed aperture proximate its lower end
   a second sheath member slidably disposed and spring biased away relative to said first sheath member wherein the combined lengths of said sheath members are greater than the length of said needle; and said second sheath member is provided with an upper and a lower aperture;
   means for temporarily immobilizing said second sheath member relative to said first sheath member at a plurality of locations; and,
   a latching unit pivotally secured to said syringe body and comprising a latching lever whose upper end forms a lever handle and whose lower end is provided with a catch member which projects inwardly towards said apertures.

2. The apparatus as in claim 1 further including:
   means for permanently immobilizing said second sheath member relative to said first sheath member.

3. The apparatus as in claim 2 wherein the means for permanently immobilizing said second sheath member relative to said first sheath member is engageable at a plurality of locations.

4. The apparatus as in claim 1 wherein the outer end of said catch member is dimensioned to be received in said apertures.

5. The apparatus as in claim 4 wherein the catch member is further provided with a deformable tang which is spaced from the outer end of the catch member.

6. The apparatus as in claim 5 wherein the deformable tang is adapted to be forced through the radial aperture in said first sheath member when said outer end of the catch member is disposed in a selected one of the upper and lower apertured in the second sheath member for permanently immobilizing the second sheath member relative to the first sheath member.

* * * * *